United States Patent
Barker

(10) Patent No.: US 12,280,269 B2
(45) Date of Patent: Apr. 22, 2025

(54) MOBILE OCULAR LIGHT THERAPY

(71) Applicant: Andrew John Barker, Calgary (CA)

(72) Inventor: Andrew John Barker, Calgary (CA)

( * ) Notice: Subject to any disclaimer, the term of this patent is extended or adjusted under 35 U.S.C. 154(b) by 179 days.

(21) Appl. No.: 18/343,450

(22) Filed: Jun. 28, 2023

(65) Prior Publication Data

US 2024/0226595 A1 Jul. 11, 2024

Related U.S. Application Data

(60) Provisional application No. 63/438,238, filed on Jan. 10, 2023.

(51) Int. Cl.
*A61N 5/06* (2006.01)

(52) U.S. Cl.
CPC ........ *A61N 5/06* (2013.01); *A61N 2005/0652* (2013.01); *A61N 2005/0663* (2013.01); *A61N 2005/0666* (2013.01)

(58) Field of Classification Search
CPC .............. A61N 5/06; A61N 2005/0652; A61N 2005/0663; A61N 2005/0666; A61N 5/0618; A61N 5/00; A61N 2005/0626; A61N 2005/0662
See application file for complete search history.

(56) References Cited

U.S. PATENT DOCUMENTS

| | | | |
|---|---|---|---|
| 6,266,476 B1 * | 7/2001 | Shie | F21S 43/249 359/566 |
| 7,678,140 B2 | 3/2010 | Brainard | |
| 9,442,346 B2 | 9/2016 | Gantz et al. | |
| 9,464,796 B2 | 10/2016 | Shoemake et al. | |
| 9,593,842 B2 | 3/2017 | Shoemake et al. | |

(Continued)

FOREIGN PATENT DOCUMENTS

| | | |
|---|---|---|
| CA | 3089860 A1 | 2/2022 |
| CN | 111538171 | 8/2020 |

(Continued)

OTHER PUBLICATIONS

Desan, P. et al., A controlled trial of the Litebook light-emitting diode (LED) light therapy device for treatment of Seasonal Affective Disorder (SAD), BMC Psychiatry, Aug. 7, 2007, pp. 1-8, BioMed Central Ltd. (http://www.biomedcentral.com/1471-244X/7/38).

*Primary Examiner* — Scott Luan
(74) *Attorney, Agent, or Firm* — Bennett Jones LLP

(57) ABSTRACT

Aspects of the present disclosure allow for a more efficient way to provide ocular light treatment therapy to a subject operating a computing device. The apparatus is configured to be coupled to a computing device. The light-emitting assembly comprises a housing with a light-emitting aperture, at least one light emitting diode (LED) configured to emit light having a component of spectral emission in a spectral region with a wavelength range of 435 nm to 500 nm, wherein at least one third of total power emitted by the at least one LED is in the spectral region, and a lens or mirror configured to collect the emitted light and project a beam of the emitted light through the light emitting aperture onto eyes of a subject viewing a display of the computing device; and a mounting bracket attached to the housing and configured to be removably attached to the computing device.

17 Claims, 9 Drawing Sheets

(56) References Cited

U.S. PATENT DOCUMENTS

| | | | |
|---|---|---|---|
| 9,715,163 B2 | 7/2017 | Williams | |
| 9,889,314 B2 | 2/2018 | Kim et al. | |
| 9,925,390 B2 | 3/2018 | Yehezkel | |
| 9,930,235 B2 | 3/2018 | Gantz et al. | |
| 9,943,700 B2 | 4/2018 | Pederson et al. | |
| 10,252,079 B2 | 4/2019 | Savage | |
| 10,265,540 B2 | 4/2019 | Yehezkel | |
| 10,315,043 B2 | 6/2019 | Pugh et al. | |
| 10,397,460 B2 | 8/2019 | Gantz et al. | |
| 10,503,205 B2 | 12/2019 | Spevak | |
| 10,533,714 B2 | 1/2020 | Rowles et al. | |
| 10,564,519 B2 | 2/2020 | Penaflor et al. | |
| 10,812,696 B2 | 10/2020 | Gantz et al. | |
| 11,007,375 B2 | 5/2021 | Yamakawa et al. | |
| 2005/0197681 A1* | 9/2005 | Barolet | A61N 5/0616 607/86 |
| 2007/0150031 A1* | 6/2007 | Barker | A61N 5/0618 606/4 |
| 2012/0271384 A1* | 10/2012 | Muehlemann | A61N 5/0618 607/90 |
| 2013/0338737 A1 | 12/2013 | Pederson et al. | |
| 2018/0221683 A1* | 8/2018 | Kang | F21V 23/02 |
| 2018/0345034 A1* | 12/2018 | Butzloff | A61N 5/0618 |
| 2020/0108272 A1 | 4/2020 | Bahmani | A61N 5/0622 |
| 2021/0176841 A1* | 6/2021 | Borra | H05B 47/17 |

FOREIGN PATENT DOCUMENTS

| | | |
|---|---|---|
| KR | 101385707 | 12/2013 |
| RU | 2189168 | 9/2002 |

\* cited by examiner

MOBILE OCULAR LIGHT THERAPY

CROSS-REFERENCE TO RELATED APPLICATIONS

This application claims priority to U.S. Provisional Patent Application No. 63/438,238, entitled "MOBILE OCULAR LIGHT THERAPY DEVICE," filed Jan. 10, 2023, the disclosure of which is hereby incorporated by reference in its entirety.

TECHNICAL FIELD

The present disclosure generally relates to apparatus and system for handheld light therapy devices, and more particularly, to handheld light therapy devices coupled to a computing device to provide ocular light treatment therapy to a subject operating the computing device.

INTRODUCTION

Light therapy has become an increasingly popular treatment for depression and a range of other neuropsychiatric conditions. Light therapy may be defined as exposure to daylight or specific wavelengths of light for a prescribed amount of time in order to treat light deficient disorders. It has been proven that treatments involving shining light directly towards a subject's eyes will alleviate or cure light deficient disorders including Seasonal Affective Disorder (SAD), circadian sleep disorders and circadian disruptions associated with jet-lag, shift-work, PMS, eating disorders, and bulimia. Light therapy has also been shown effective for fatigue management.

Light therapy devices incorporating light emitting diodes (LEDs) are widely available to treat light deficient disorders. Typical light therapy devices incorporate LEDs that emit white light with various color temperatures, including cool white light with a relatively high content of blue light. As an example, light therapy devices may emit blue or blue-green light with a component of spectral emission in a wavelength range of approximately 435 nm to 500 nm since light in this range has been found to be of maximal potency in the regulation of the human circadian and photo neural systems via ocular exposure.

In some examples, light therapy devices are portable, but require a connection to a wall outlet or incorporate a rechargeable battery due to the large consumption of power needed to emit the light. These smaller sized light therapy devices are convenient to use while a subject is reading, watching television, or using a computing device (e.g., desktop computer, tablet, smartphone, portable game console, or a PDA) since these can be placed on a suitable surface or table next to the subject and the computing device. However, when there is no suitable surface or table, then the use of a separate light therapy device to deliver light therapy while reading, watching television, or using a computing device is less practical since the subject needs to hold the light therapy device.

In some cases, a computing device such as a mobile communication device or tablet may itself be used to deliver ocular light therapy to a user. However, dedicating a device screen (or display) of the communication device itself to act as a light therapy device precludes the simultaneous use of the device screen on the computing device for tasks such as checking emails, texts, watching media, or browsing the website. In addition, the normal irradiance of therapeutically effective light emanating from the display of a typical mobile communication device or tablet at a normal viewing distance of approximately 30 cm is almost two orders of magnitude less than that provided by most light therapy devices. This means that an extremely long duration of exposure is required to achieve equivalent therapeutic benefits.

In addition, clip-on selfie lights that are powered by an internal rechargeable battery to provide additional lighting for a camera or other imaging purposes are also widely available. These clip-on selfie lights are generally adaptable to different size mobile communication devices since the clip-on selfie lights attach to the edge of the mobile communication devices or cases of the mobile communication devices via a clip. However, many of these clip-on selfie lights surround the camera lens thereby obscuring part of a display of the mobile communication device when attached. In addition, these clip-on selfie lights emit white light in a relatively wide beam having an angular width at 50% intensity of approximately 60 degrees. This wide light beam is useful for even illumination during short range photography, but is much wider than needed for the efficient delivery of personal ocular light therapy since most of the LED power required to create such a wide beam is wasted due to the light not entering the eyes of a user. In addition, prolonged use of such a wide beam of light in close proximity to other people is impractical due to creating a disturbance to the other people.

Furthermore, protective cases for mobile communication devices have also incorporated LEDs to provide additional lighting for selfies and other imaging purposes and have also been widely available. However, similar to the light therapy limitations with the clip-on selfie lights, these types of accessory products are generally powered by an internal rechargeable battery and are neither designed nor intended to be used for light therapy.

In addition, even though this type of treatment is generally safe, negative effects may occur. As a consequence of light therapy, subjects may complain of irritability, headache, eye strain, sleep disturbances, and insomnia. Therefore, determining the appropriate dose and timing of light is essential in order to diminish the occurrence of side effects.

Accordingly, there exists a need for a mobile ocular light therapy device that overcomes the above-mentioned limitations and enables delivery of light therapy from a computing device while the computing device is operated by a user under normal conditions. In addition, there is a need to provide a mobile ocular light therapy device that may accommodate computing devices of any size or shape. It would also be helpful to provide a mobile ocular light therapy device with high optical efficiency and low power consumption to draw power directly from a battery of the mobile communication device with minimal impact on the battery life of the computing device. There also exists a need to provide a mobile ocular light therapy device that delivers personal light therapy by projecting a well-defined, relatively narrow beam of light onto the eyes of a user while the user is operating a computing device.

SUMMARY

The following presents a simplified summary of one or more aspects in order to provide a basic understanding of such aspects. This summary is not an extensive overview of all contemplated aspects, and is intended to neither identify key or critical elements of all aspects nor delineate the scope of any or all aspects. Its sole purpose is to present some concepts of one or more aspects in a simplified form as a prelude to the more detailed description that is presented later.

The subject matter described in this disclosure can be implemented in an apparatus coupled to a computing device for providing ocular light therapy. The apparatus includes a light-emitting assembly comprising: a housing with a light-emitting aperture, at least one light emitting diode (LED) configured to emit light having a component of spectrum emission in a spectral region with a wavelength of 435 to 500 nm, wherein at least one third of the total power emitted by the at least one LED is in the spectral region, and a lens or mirror configured to collect the emitted light and project a beam of the emitted light through the light-emitting aperture onto the eyes of a subject viewing a display of the computing device; and a mounting bracket attached to the housing and configured to be removably attached to the computing device or a case of the computing device.

The subject matter described in this disclosure can also be implemented in an apparatus configured to be coupled to a computing device for providing ocular light therapy. The apparatus includes a light-emitting assembly comprising: a housing with a light-emitting aperture; at least one light emitting diode (LED) configured to emit light, and a lens or mirror configured to collect the emitted light and project a beam of the light through the light emitting aperture onto the eyes of a subject viewing a display of the computing device, wherein the projected beam of the light has an angular divergence of less than 36 degrees in both horizontal and vertical planes measured at half of a maximum intensity; and a mounting bracket attached to the housing and configured to be removably attached to the computing device or a case of the computing device.

The subject matter described in this disclosure can further be implemented in a system for providing ocular light therapy. The system comprising: a computing device; an ocular light therapy device for administering ocular light treatment to a subject, comprising: a light-emitting assembly comprising: a housing with a light-emitting aperture; at least one light emitting diode (LED) configured to emit light having a component of spectral emission in a spectral region with a wavelength range of 435 nm to 500 nm, wherein at least one third of a total power emitted by the at least one LED is in the spectral region, a lens or mirror configured to collect the light and project a beam of the light onto the eyes of the subject viewing a display of the computing device; and a mounting bracket attached to the housing and configured to be removably attached to the computing device or a case of the computing device.

To the accomplishment of the foregoing and related ends, the one or more aspects comprise the features hereinafter fully described and particularly pointed out in the claims. The following description and the annexed drawings set forth in detail certain illustrative features of the one or more aspects. These features are indicative, however, of but a few of the various ways in which the principles of various aspects may be employed, and this description is intended to include all such aspects and their equivalents.

DETAILED DESCRIPTION

Figure 1A:
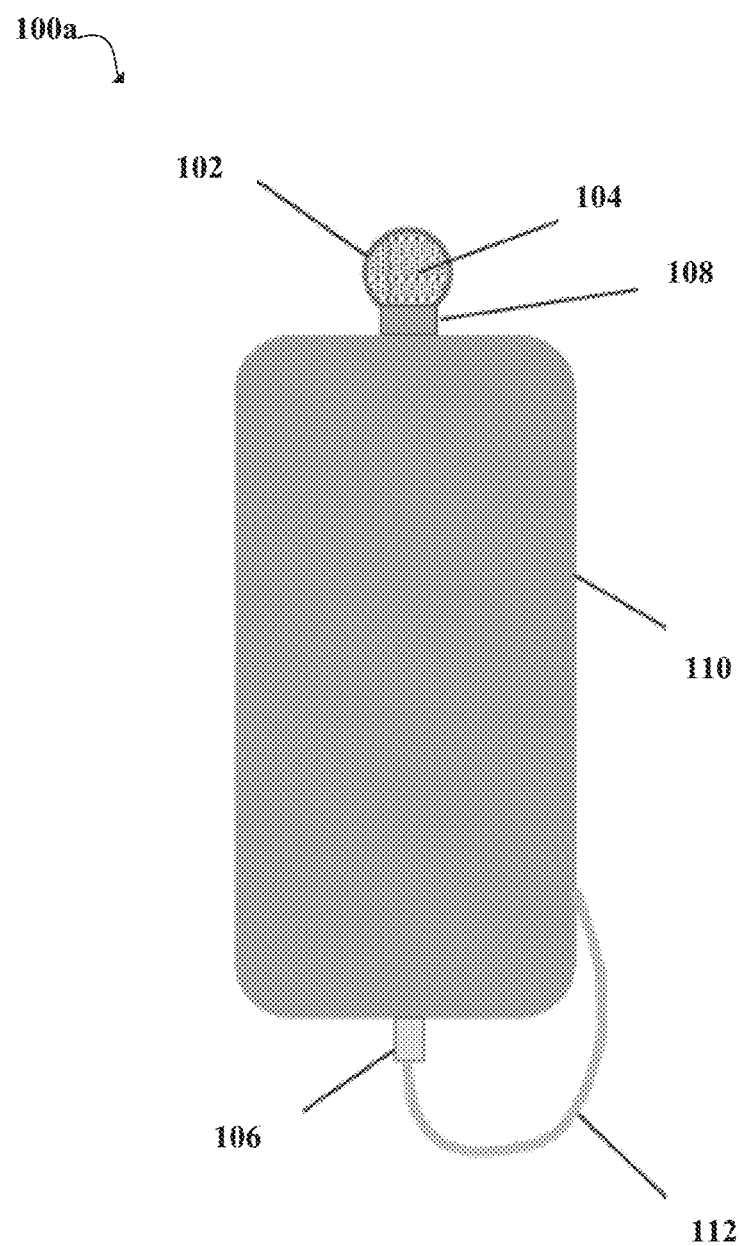
FIGS. 1A-1B are diagrams illustrating examples of front and rear views of a system for providing ocular light therapy treatment to a human subject in accordance with various aspects of the present disclosure.

The detailed description set forth below in connection with the appended drawings is intended as a description of various configurations and is not intended to represent the only configurations in which the concepts described herein may be practiced. The detailed description includes specific details for the purpose of providing a thorough understanding of various concepts. However, the concepts and related aspects described in the present disclosure may be implemented in the absence of some or all of such specific details. In some instances, well-known structures, components, and the like are shown in block diagram form in order to avoid obscuring such concepts.

Several aspects of exemplary embodiments according to the present disclosure will now be presented with reference to various systems and methods. These systems and methods will be described in the following detailed description and illustrated in the accompanying drawings by various blocks, components, circuits, processes, algorithms, etc. (collectively referred to as "elements"). These elements may be implemented using electronic hardware, computer software, or any combination thereof. Whether such elements are implemented as hardware or software depends upon the particular application and design constraints imposed on the overall system.

By way of example, an element, or any portion of an element, or any combination of elements may be implemented as a "controller" that includes one or more processors or controllers. Examples of processors or controllers include microprocessors, microcontrollers, graphics processing units (GPUs), central processing units (CPUs), application processors, digital signal processors (DSPs), reduced instruction set computing (RISC) processors, systems on a chip (SoC), baseband processors, field programmable gate arrays (FPGAs), programmable logic devices (PLDs), application-specific integrated circuits (ASICs), state machines, gated logic, discrete hardware circuits, and other suitable hardware configured to perform the various functionality described throughout this disclosure. One or more processors in the controller may execute software. Software shall be construed broadly to mean instructions, instruction sets, code, code segments, program code, programs, subprograms, software components, applications, software applications, software packages, routines, subroutines, objects, executables, threads of execution, procedures, functions, etc., whether referred to as software, firmware, middleware, microcode, hardware description language, or otherwise.

The one or more processors or controllers can be associated with a memory that stores data. The memory may also be referred to as a computer-readable medium.

Accordingly, in one or more exemplary embodiments, the functions described may be implemented in hardware, software, or any combination thereof. If implemented in software, the functions may be stored on or encoded as one or more instructions or code on a computer-readable medium. Computer-readable media includes computer storage media. Storage media may be any available media that can be accessed by a computer. By way of example, and not limitation, such computer-readable media can comprise a random-access memory (RAM), a read-only memory (ROM), an electrically erasable programmable ROM (EEPROM), optical disk storage, magnetic disk storage, other magnetic storage devices, combinations of the aforementioned types of computer-readable media, or any other medium that can be used to store computer executable code in the form of instructions or data structures that can be accessed by a computer.

In related light therapy systems, light therapy systems have included powerful light sources emitting high intensity light. In some examples, fluorescent lamps have been used for the purposes of emitting high intensities of light. These systems make it difficult for a user to look past the bright light source to more dimly lit surfaces to accomplish other tasks. In addition these lights may cause eyestrain, headache, and other discomforts. Furthermore, these commercial light therapy units are large, bulky, and cumbersome.

In other related light therapy systems, portable light therapy devices have been made into lighter and smaller hand-held sizes due to advances in LED technology. The majority of these portable light therapy devices provide facial irradiance in the range of 200 to 300 microwatts/cm$^2$ in the therapeutically effective blue region of the spectrum. At this intensity, significant therapeutic effect is achievable with exposure as short as 15 minutes. However providing irradiance at these light intensities consumes a significant amount of power such that the light therapy devices require access to an external power outlet or relatively large rechargeable batteries. These portable light therapy devices can be positioned next to a desktop computer on a desk or table to enable the administration of light therapy to a person using the desktop computer but they are inconvenient to use in conjunction with a mobile computing device if the person using the mobile computing device is moving or traveling and no support surface is available for the light therapy device. These dedicated portable light therapy devices also do not incorporate any mobile computing functionality.

Therefore, it would be helpful to have a portable light therapy system that utilizes a computing device to create a projected beam of light suitable for efficient delivery of ocular light therapy to a subject viewing a computing device. Examples of a computing device may include a personal computer, a laptop computer, a personal digital assistant (PDA), a tablet device, a cellular phone, a portable game console, a video game console, a smart display, a display, a smartphone, or any other similar functioning device.

Since the typical time a subject spends viewing the screen of a computing device is over an hour, it would be helpful to utilize this screen time by providing simultaneous exposure to ocular light therapy. For example, light therapy may be provided to the subject while the subject is viewing their computing device by emitting therapeutically effective light at a lower intensity for a longer period of time, which would mitigate power consumption issues in related light therapy systems. It would further be helpful if a light therapy device had a high optical efficiency and low power consumption, and was packaged in a small size such that the light therapy device can be removably attached to any type of computing device to provide an ocular light therapy device that is accessible during normal operation of the computing device and/or draw power from the computing device with minimal depletion of the battery in the computing device.

Continuous exposure to ocular light therapy for approximately 1.5 hours has been proven to provide significant therapeutic effect with as little as 20 microwatts/cm$^2$ using a therapeutically effective light, which encompasses blue and blue-green as well as blue rich and blue-green rich light. In addition, providing irradiance at a level well below 200 microwatts/cm$^2$ also reduces the risk of visually distracting glare from a relatively small light-emitting assembly.

FIG. 1A is a diagram illustrating a front view of an exemplary embodiment of a system 100a for providing ocular light treatment therapy to a human subject. While pertinent features are shown, those of ordinary skill in the art will appreciate from the present disclosure that various other features have not been illustrated for the sake of brevity and so as not to obscure more pertinent aspects of the example implementations disclosed herein. To that end, as a non-limiting example, in some implementations, the system 100a includes a light-emitting assembly 102 attached to a mobile communication device 110 via a bracket 108.

As shown in FIG. 1A, the light-emitting face 104 of the light-emitting assembly 102 faces in the same direction as a display of the mobile communication device 110. The length of the bracket 108 determines the separation between the light-emitting assembly 102 and a display of the mobile communication device 110. In other words, the greater the separation between the light-emitting assembly 102 and the screen of the mobile communication device 110, the lower the risk of visual distraction caused by a therapeutic light to a subject viewing the screen of the mobile communication device 110. It is an advantage of the disclosure that the light-emitting face 104 is intended for positioning at an angle in the field of view of the human subject so that the light is emitted with an intensity and directionality that makes it possible for the human subject to perform various activities on the mobile communication device without being unduly bothered or distracted by the emitted light. This also allows the light therapy treatment to have a longer duration than compared to similar light therapy devices that emit light of a high intensity for a relatively short time period. In other words, the subject may be subjected to light treatment at a lower intensity for a longer period of time, which may mitigate side effects of light therapy devices using high intensity light. In addition, the intensity and directionality of the emitted light leaves other persons in the room unaffected.

Figure 1B:
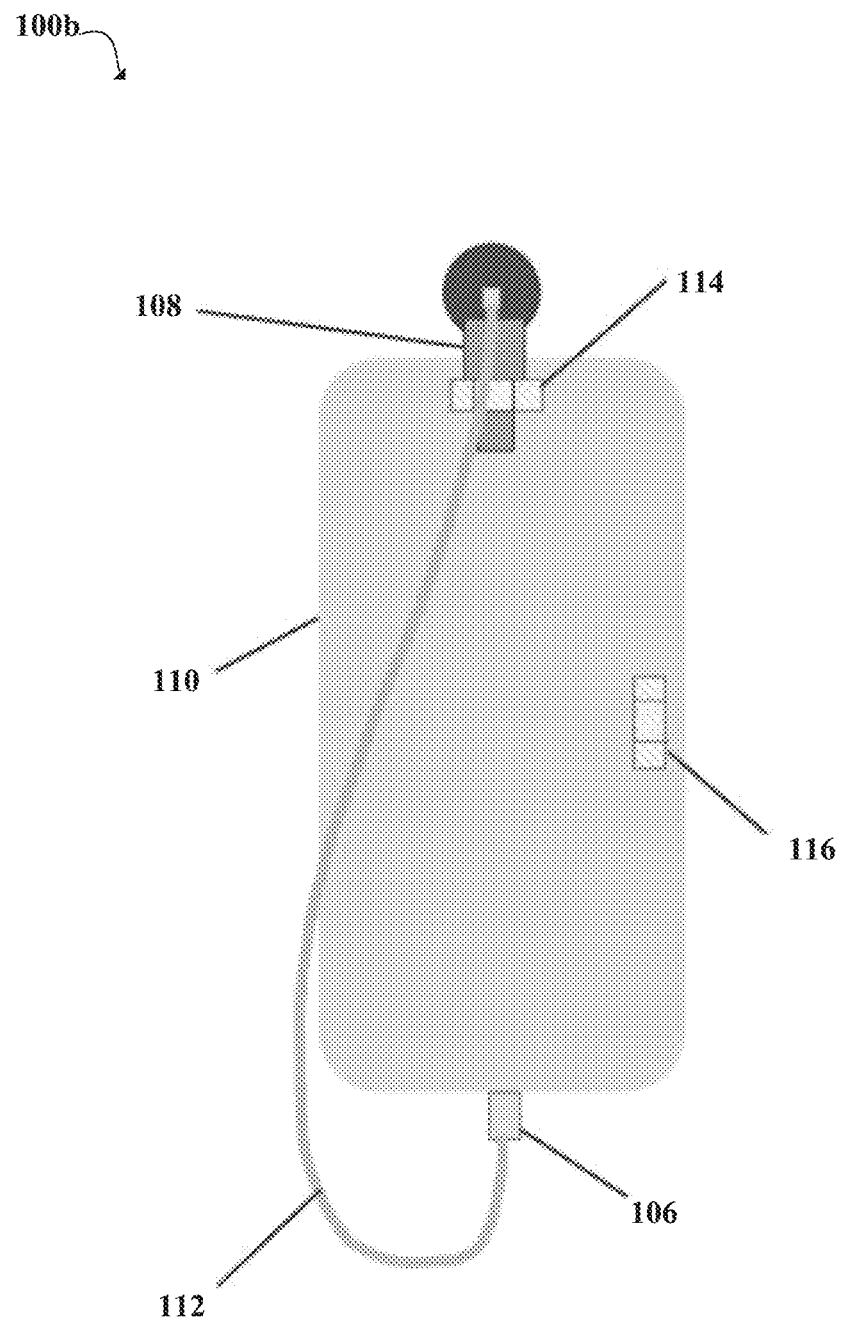

FIG. 1B is a diagram illustrating a rear view of an exemplary embodiment of a system 100b for providing ocular light therapy treatment to a human subject. While pertinent features are shown, those of ordinary skill in the art will appreciate from the present disclosure that various other features have not been illustrated for the sake of brevity and so as not to obscure more pertinent aspects of the example implementations disclosed herein. To that end, as a non-limiting example, in some implementations, the system 100*b* includes a light-emitting assembly 102 attached to a mobile communication device 110 via a bracket 108.

As shown in FIG. 1B, a mounting bracket 114 is mounted to a rear surface of the mobile communication device 110 or a protective sleeve or case of the mobile communication device 110. The mounting bracket 114 is designed to provide easy insertion and removal of the bracket 108 while providing sufficient retentive force to prevent inadvertent disengagement of the bracket 108 from the mounting bracket 114. In some examples, the mounting bracket 114 may be configured to be coupled to bracket 108 adhesively, magnetically, or by any other suitable means.

In some examples, an additional mounting bracket 116 may be positioned adjacent to a long edge of the mobile communication device 110 to be more convenient to use when the mobile communication device 110 is viewed in a landscape orientation.

In some examples, the bracket 108 can alternatively be configured as a spring clip that grips edges of a front and rear surface of the mobile communication device 110. In some examples, the bracket 108 can be attached to the rear of the mobile communication device 110 or attached to a protective sleeve or protective case of the mobile communication device 110 using one or more suction cups.

In some examples, the bracket 108 may be configured to allow the light-emitting assembly 102 (not shown in FIG. 1B) to remain attached to the mobile communication device 110 and be movable when not in use by folding, rotating, or sliding part of the bracket 108 to enable re-positioning of the light-emitting assembly 102 to a location at the rear of the mobile communication device 110 or its case so that neither the light-emitting assembly 102 nor the bracket 108 remains visible from the front of the mobile communication device 110.

In some examples, the light-emitting assembly 102 may further comprise a power receiver configured to draw power for the light-emitting assembly 102 from the mobile communication device 110. For example, a cable 112 is terminated with a connector 106 that is compatible with a charging port (or computer interface port) on the mobile communication device 110 to provide power to the light-emitting assembly 102 from the battery of the mobile communication device 110. For example, the charging port may be a USB-A, USB-C, micro-USB, an Apple Lightning port, or any other suitable port.

The cable 112 may also enable communication between the mobile communication device 110 and the light-emitting assembly 102. In some examples, the cable 112 is permanently wired into the light-emitting assembly 102. In some cases, the cable 112 can be configured with connectors at each end to allow a detachable connection to a compatible socket mounted on the light-emitting assembly 102. For example, the light-emitting assembly 102 may be adapted to be computer controlled through a computer interface such as the charging port such that a subject may set the emitted light intensity using the mobile communication device 110.

In some examples, the light-emitting assembly 102 may draw power inductively from the mobile communication device 110 by means of a suitably located inductive receiver integrated with the bracket 108 of the light-emitting assembly 102. This would eliminate the need for a cable connection to draw power from the mobile communication device 110.

In some examples, a subject may control the functioning of the light-emitting assembly 102 utilizing a user interface of the mobile communication device 110. Specifically, the subject may adjust various parameters such as the exposure time, the shape of the emitted light spectrum, the shape, the direction, or the intensity of the emitted light, etc. In another example, the mobile communication device 110 may further be adapted to execute different light exposure programs for varying intensity and spectral shape as a function of time. These programs may be stored by a subject or downloaded and uploaded via a network.

In some examples, the mobile communication device 110 may simultaneously perform other tasks that are unrelated to light therapy. For example, the subject may use the mobile communication device 110 under normal operation circumstances such as watching a video, or browsing the internet during treatment with the light therapy apparatus. Utilizing the processors on the mobile communication device 110 eliminates the need for a separate or dedicated computer in the light-emitting assembly 102, which further decreases the size and weight and cost of the light-emitting assembly 102.

In some examples, the light-emitting assembly 102 may draw power from a rechargeable battery within a housing of the light-emitting assembly. The capacity of the battery does not need to be large due to the lower power requirement of the light-emitting assembly 102 as compared to other related light therapy devices.

In some examples, the light-emitting assembly 102 is designed to project a sharply-defined beam of light towards a face of the subject. In some examples, the beams of light diverging from the light-emitting aperture may have a divergence that is sufficiently low so that at a typical viewing distance of 30 cm, neither the full width nor the full height of the projected beam of light measured between the locations at each side of the beam where the intensity has fallen to one half of maximum intensity is greater than the width or height of a human head. Specifically, in the context of this example, measuring half of maximum intensity refers to a method of establishing boundaries for distance and/or angular measurement. For instance, with reference to example 700 from FIG. 7, when measuring a beam strength in a two-dimensional plane (X and Y axis) that traverses the beam at a distance (e.g., a typical viewing distance of 30 cm) from the light-emitting assembly 102, the maximum intensity in a center of the beam is measured with the intensity decreasing from the center of the beam in any direction along the two-dimensional plane. Thus, the boundaries of the beam is where half of the maximum intensity is measured. For example, the beam of light projected onto the eyes of the subject at a distance of 30 cm from the light-emitting aperture has a height and width of less than 20 cm at half of a maximum intensity. In some examples, the projected beam of light has an angular divergence of less than 36 degrees in both horizontal and vertical planes measured at a half of a maximum intensity. Limiting the width of the projected beam of light in this way minimizes the risk that light from the light-emitting assembly could be distracting for other persons in the vicinity of the subject.

The bracket 108 permits adjustment of a direction of the projected beam of light such that the beam of light is centered on an average location of the eyes of the user viewing a screen of the mobile communication device 110. The eyes of the subject viewing the screen of the mobile communication device 110 will typically be close to a central axis of the screen at a viewing distance of approximately 30 cm. In some examples, the bracket 108 can be pre-formed to aim the projected beam of light in the required direction or can be configured to permit adjustment of the projected beam to suit the individual preferences of the subject. In addition, further adjustment of the direction of the projected beam of light can be achieved by minor adjustment of the orientation of the mobile communication device 110.

Once the light-emitting assembly 102 is attached to the mobile communication device 110, the light-emitting assembly 102 is positioned a short distance away from one edge of the mobile communication device and the light-emitting face of the light-emitting assembly 102 is facing in the same direction as the display of the mobile communication device 110. The light-emitting assembly includes at least a lens to collect light from a single LED powered via a current control circuit and project an image of the LED in a forward direction through the light-emitting face of the light-emitting assembly. Additional optical components may be placed in front of the lens to expand the projected image of the LED to create a projected beam of light suitable for efficient delivery of ocular light therapy to the eyes of a subject viewing the mobile communication device 110 from a distance of approximately 30 cm.

In some examples, a light-emitting assembly 102 with high optical efficiency, low power consumption, and a small size can be permanently attached to or integrated into a housing of the mobile communication device 110. The permanently attached or integrated light-emitting assembly 102 may include a deployable mechanism to allow movement of the light-emitting assembly 102 between a stored state and an active state at a suitable distance from the display of the mobile communication device 110.

It will be appreciated by those skilled in the art that the elements of the system 100a and 100b are not limited to those depicted in FIGS. 1A and 1B. The systems 100a and 100b may include more or less hardware elements than those depicted. Further, hardware elements may share functionality and still be within various embodiments described herein. It should be noted that even though the disclosure references a mobile communication device, the mobile communication device is an illustrative example only and that any suitable computing device such as a tablet, laptop, personal digital assistants (PDAs), portable video game console, a smartphone, a cellular phone, or the like could be used.

Figure 2:
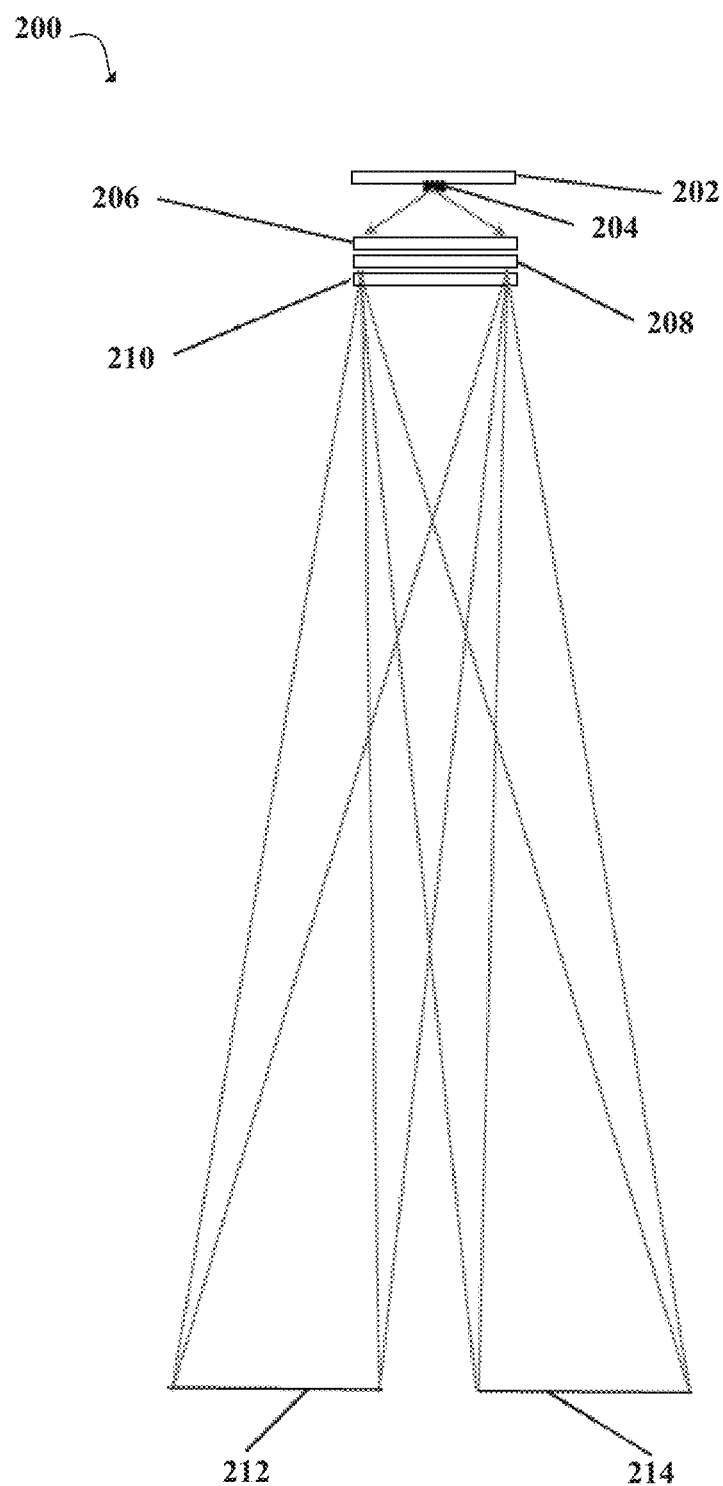
FIG. 2 is a diagram illustrating an optical schematic of a light-emitting assembly in accordance with various aspects of the present disclosure.

FIG. 2 is a diagram illustrating an embodiment of a system 200 for providing ocular light therapy treatment to a human subject. While pertinent features are shown, those of ordinary skill in the art will appreciate from the present disclosure that various other features have not been illustrated for the sake of brevity and so as not to obscure more pertinent aspects of the example implementations disclosed herein. To that end, as a non-limiting example, in some implementations, the system 200 includes at least a circuit board 202, at least one LED 204, a lens 206, an optical beam divider 208 (optional), and an optical diffuser 210 (optional).

The system 200 may be configured to create one or more light patches on a subject as shown below in FIGS. 5A-5C. For example, a system 200 with an optical beam divider may create two light patches for each eye in a first configuration 500a shown in FIG. 5A. As another example, a system 200 without the optical beam divider 208 may create a single light patch as shown in a second configuration 500b and a third configuration 500c shown in FIGS. 5B and 5C, respectively.

In some examples, at least one LED 204 is mounted on a circuit board 202 that includes a current control. The at least one LED 204 is configured to emit light into a wide angle to be collected by a lens 206. The lens 206 is configured to form and focus an image of the LED 204 on the optical axis of the lens 206 at a distance of approximately 30 cm. The approximate distance of 30 cm is chosen because that is the typical distance between the eyes of a subject viewing a computing device and a front display of the computing device. In some examples, an optical diffuser 210 may be included in the light-emitting assembly to increase the size or improve the uniformity of the LED images by widening and smoothing the LED images.

Figure 5C:
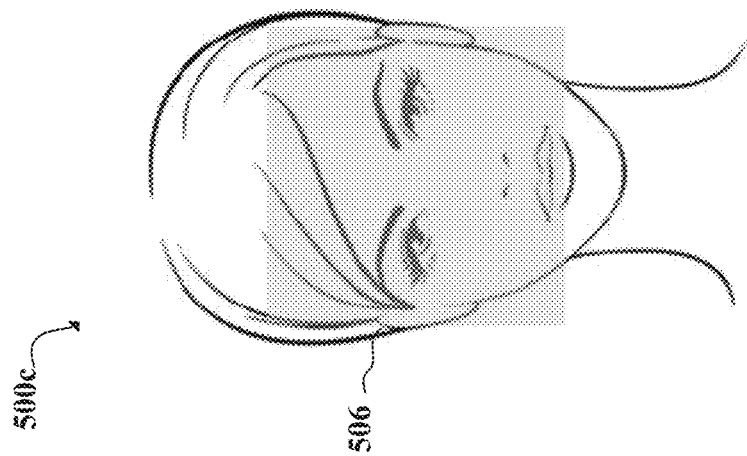
FIGS. 5A-5C are diagrams illustrating examples of distinct light patches projected onto a human subject in accordance with various aspects of the present disclosure.
Figure 5B:
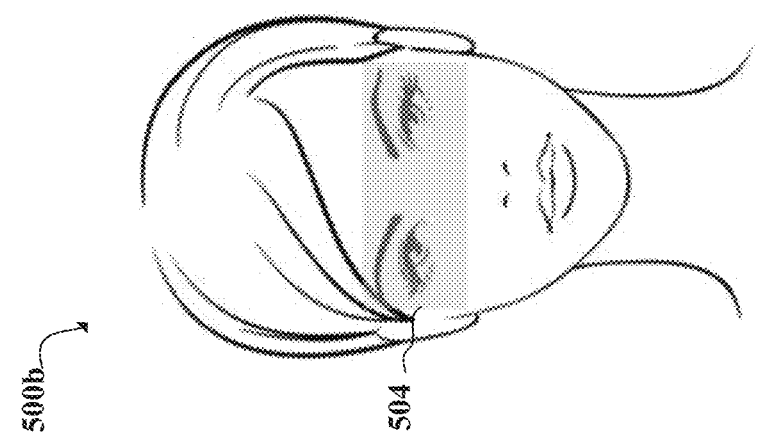
Figure 5A:
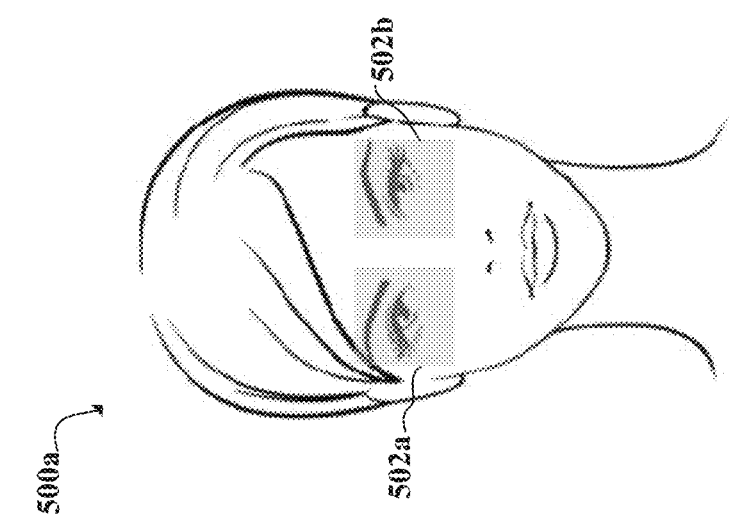

As shown in a first configuration 500a shown in FIG. 5A, the system 200 may create two light patches for each eye, in a first example, the system 200 may include an optical beam divider 208 configured to split the image-forming light into two diverging beams (e.g., a first beam for the left eye and a second beam for the right eye). The divergence angle of the two beams creates two separate images 212, 214 of the LED at a distance of approximately 30 cm with a separation approximately equal to the average human interpupillary distance. In some examples where the optical beam divider 208 is not part of the system 200, the at least one LED 204 may consist of two LEDs separated by a small distance such that the lens 206 creates two diverging beams from the two separate LEDs. In some examples where the optical beam divider 208 is not part of the system 200, the lens 206 may be custom configured as two half lenses joined together with a small separation between the optical centres of each half lens such that the custom lens is configured to create two diverging beams from a single LED 204. In some examples, the two half lenses joined together with a small separation may be tooled as a custom Fresnel lens.

The LED 204 can be of any type capable of providing sufficient optical power to create therapeutically effective irradiance in the LED images. In order to create therapeutically effective irradiance, the LED emission spectrum must include a significant component of blue or blue-green light in the range of 435 nm to 500 nm. In some examples, the light-emitting assembly is further configured to emit the light to provide an irradiance within a range of 50 to 200 microwatts/cm$^2$ in the spectral range of 435 nm to 500 nm at a distance of 30 cm from the light-emitting aperture. In some examples, the LED 204 may have a square emitting area such that the projected LED images are similar to the two light patches 502a, 502b as shown in FIG. 5A.

In some examples, the LED 204 may be configured to emit blue or blue/green light with an emission spectrum exhibiting a peak at a wavelength in the range from 450 nm to 480 nm. In some examples, the LED 204 may be configured to emit light having a component of spectrum emission in a spectral region with a wavelength of 435 nm to 500 nm, wherein at least one third of the total power emitted by the LED 204 is in the spectral region from 435 nm to 500 nm. Light with a significant component of emission in the blue-green region of the spectrum has been found to be particularly therapeutically effective, even at relatively low intensity levels. Blue light and blue-green light in this region of the spectrum has been proven to provide maximal therapeutic efficacy while creating less visual glare than green or white light due to the relatively low luminous efficacy of blue light. Specifically, blue light has been found to be particularly effective for suppressing melatonin which can improve alertness and is helpful in treating seasonal affective disorder (SAD) and certain other conditions such as "jetlag" and various other modulations of the circadian rhythm to improve the general health and well-being of the subject.

The lens 206 may also be of any form, but, for high optical efficiency, the focal length of the lens 206 must be a small fraction of the diameter of the lens. In some examples, the lens 206 is an aspheric Fresnel lens with a diameter that is at least three times the focal length of the lens 206. In some examples, the lens 206 is an aspheric Fresnel lens with a focal length of approximately 6 mm and a diameter of approximately 30 mm.

In some examples, the optical beam divider 208 is a Fresnel beam divider (as will be described in more detail in FIG. 3).

The optical diffuser 210 may be of any form, but, for high optical efficiency, the optical diffuser 210 may be a lenticular array, a micro-lens array, or an engineered diffuser that creates a sharply-defined expanded pattern with a high transmission and little wasted scattered light. The lens 206, optical beam divider 208, and optical diffuser 210 can each be manufactured as thin, lightweight components and can be replicated at low cost in high volumes.

In some examples, the system 200 may include an optical deflector configured to deflect the projected beam of light such that the projected beam of light is centered on the eyes of the subject viewing the display of the computing device. In some examples, the optical deflector is a Fresnel prism.

As a non-limiting example, the LED 204 may have an emitting area of approximately 1 mm×1 mm and is configured to emit blue rich light with a spectrum that peaks at approximately 460 nm, the lens 206 is a Fresnel lens with a focal length of approximately 6 mm and diameter of approximately 30 mm, and the optical beam divider 208 creates a pair of beams diverging at an angle of approximately 12 degrees. At a distance of 30 cm, the lens 206 forms an image of LED 204 with a magnification of 49 and the optical beam divider 208 separates the two LED images by a distance of approximately 64 mm. Thus, in this example, the system 200 projects two identical patches of light with an approximate size of 49 mm×49 mm that are separated by an average human interpupillary distance.

In some examples, the circuit board 202 with LED 204 and associated current control circuitry, including the lens 206, optical beam divider 208, and optical diffuser 210 may be packaged into an enclosure approximately 30-40 mm in diameter and 12 mm thick. In some examples, the enclosure may include an on and off switch. The enclosure may be attached to a mounting bracket (e.g., the bracket 108 shown in FIGS. 1A and 1B) that can be removably attached to a computing device (e.g., the mobile communication device 110 shown in FIGS. 1A and 1B).

Figure 3:
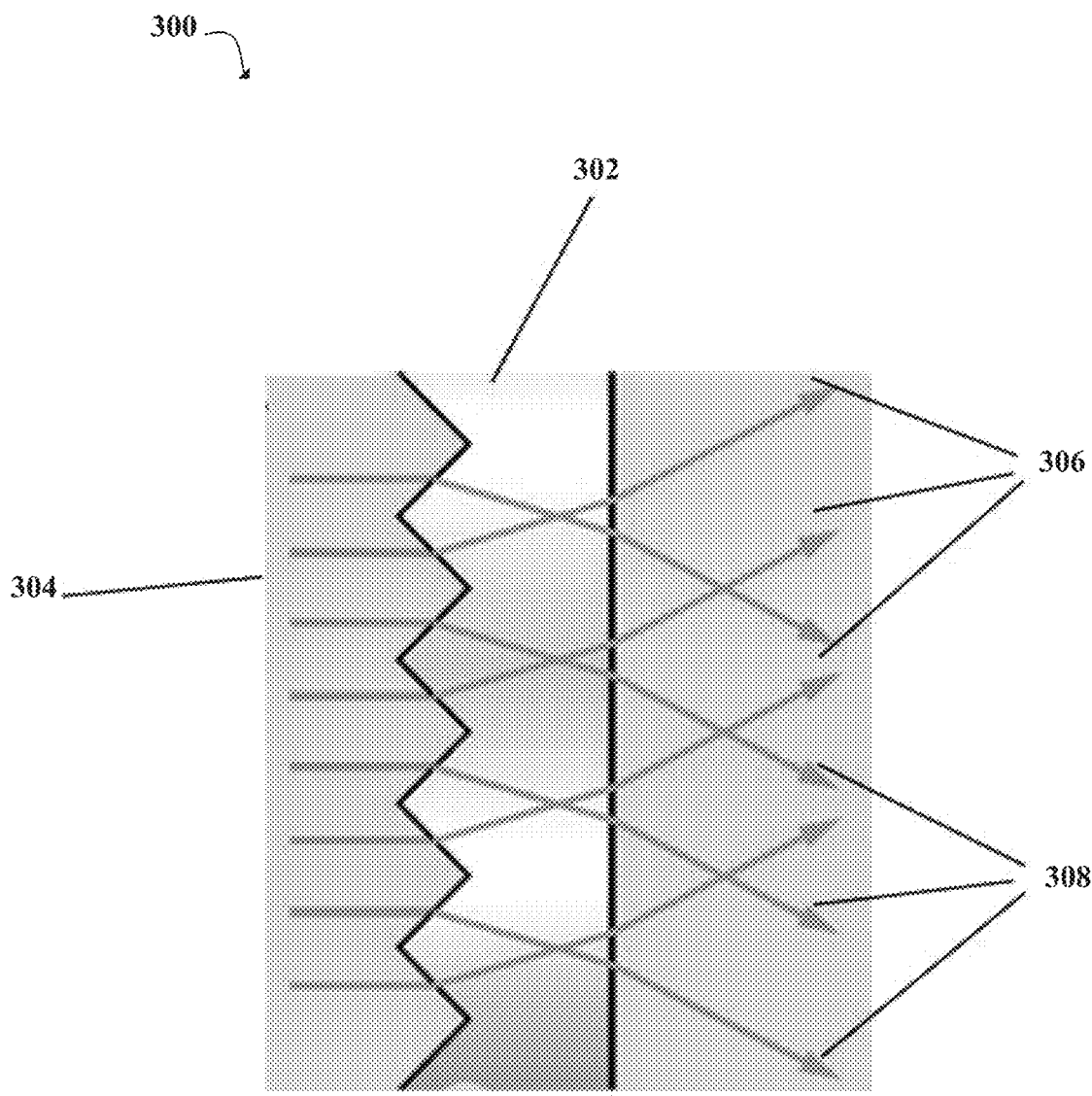
FIG. 3 is a diagram illustrating an example of a beam divider in accordance with various aspects of the present disclosure.

FIG. 3 shows an example 300 of a beam dividing action of a Fresnel beam divider 302. While pertinent features are shown, those of ordinary skill in the art will appreciate from the present disclosure that various other features have not been illustrated for the sake of brevity and so as not to obscure more pertinent aspects of the example implementations disclosed herein. As shown in the example 300 from FIG. 3, an incoming beam 304 is divided by alternate facets on the Fresnel beam divider 302 to create a pair of diverging beams 306, 308.

Figure 4:
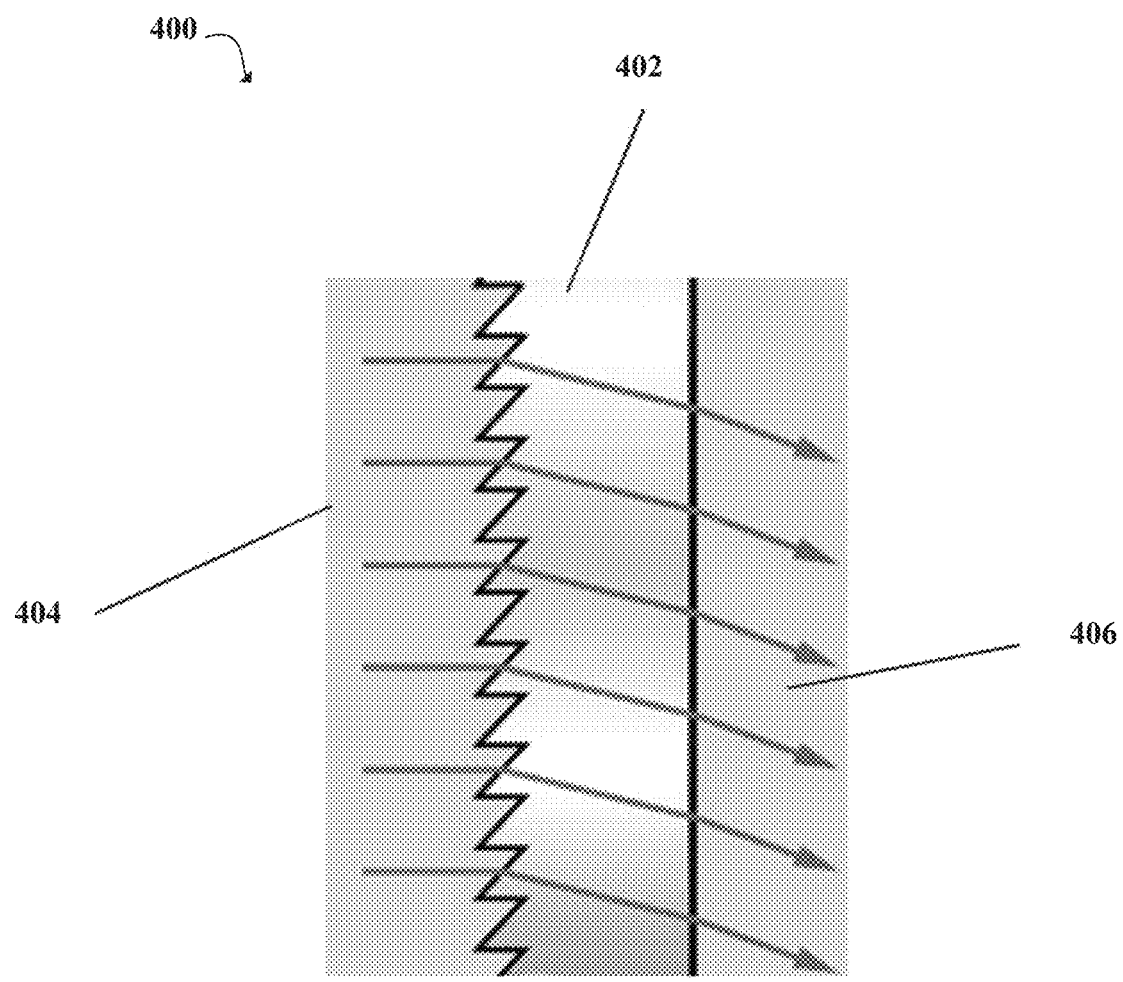
FIG. 4 is a diagram illustrating an example of a beam deflector in accordance with various aspects of the present disclosure.

FIG. 4 shows an example 400 of a beam deflecting action of a Fresnel prism. While pertinent features are shown, those of ordinary skill in the art will appreciate from the present disclosure that various other features have not been illustrated for the sake of brevity and so as not to obscure more pertinent aspects of the example implementations disclosed herein.

In some examples, a light-emitting assembly may include an optical deflector in front of the Fresnel lens to deflect the projected beam of light through a pre-determined angle so that the projected beam of light is centered on the average location of the eyes of a subject viewing the screen of the computing device. In some examples, the optical deflector is a Fresnel prism.

As shown in the example 400 from FIG. 4, an incident beam 404 is deflected by facets on the Fresnel prism to create deflected beam 406. In some examples, the beam deflector 402 provides a beam deflection of approximately 18 degrees in a direction orthogonal to the beam divergence provided by the beam divider. The facet structures required for beam deflector 402 and beam divider 302 can be created on opposite sides of a single optical component.

FIGS. 5A-5C are diagrams illustrating examples of distinct light patches projected onto a human subject using a light-emitting assembly in accordance with various aspects of the present disclosure. While pertinent features are shown, those of ordinary skill in the art will appreciate from the present disclosure that various other features have not been illustrated for the sake of brevity and so as not to obscure more pertinent aspects of the example implementations disclosed herein.

FIG. 5A shows a first configuration 500a in which separate light patches 502a, 502b are centered on each eye of the subject. Compared to the second and third configurations 500b, 500c shown in FIGS. 5B and 5C, the first configuration 500a requires a lower LED power to deliver a given dose of light therapy. The system 200 shown in FIG. 2 may project the separate light patches 502a, 502b by using a beam divider shown in FIG. 5A.

For example, in order to create the separate light patches 502a, 502b, the combination of the lens 206, optical beam divider 208, and optical diffuser 210 can collect and transmit approximately one third of a total optical output P of the LED 204. The total area of the two separate light patches 502a, 502b of approximately 4.9 cm×4.9 cm is 48 cm$^2$. Assuming a target irradiance of 50 microwatts/cm$^2$, to ensure a margin of performance, the calculation is: P/3=48*50 microwatts=2.4 milliwatts. Hence, the required LED power P needed to achieve 50 microwatts/cm$^2$ is approximately 7.2 milliwatts (mW).

As an example, an LED may have a 1 mm×1 mm blue light emitter, which emits 7.2 mW of optical power with a drive current of approximately 4.4 mA. The voltage available on a mobile communication device is typically regulated at 5V. Assuming that a resistor is used in the light-emitting assembly as a LED current regulator, the power drain on the battery of the mobile communication device would be 4.4 mA*5V=22 mW. Most mobile communication device batteries have a capacity of 3,000-4,000 milliampere hour (mAh) at a voltage of approximately 3.7V so the total available energy is at least 11.000 (mWh). On that basis, the most efficient configuration for the light therapy attachment would take at least approximately 500 hours to empty a fully-charged battery of the mobile communication device. In some examples, using a current regulator device in place of the resistor would further reduce the power drain on the battery of the mobile communication device.

FIG. 5B shows a second configuration 500b in which a single light patch 504 is centered around the eyes of the subject. The second configuration 500b is similar to the first configuration 500a, but may provide a greater tolerance in terms of the light being emitted correctly to the eyes of the subject.

In order to create the single light patch 504 shown in the second configuration 500b in FIG. 5B, the beam divider is removed from the system 200 shown in FIG. 2. In some examples, a diffuser (e.g., optical diffuser 210 shown in FIG. 2) is selected to provide an asymmetric characteristic that broadens the single LED image predominantly in one direction to create the single light patch 504 with the required width at approximately 30 cm. Assuming that the single light patch 504 with dimensions of approximately 12 cm×5 cm is projected at a distance 30 cm away from the light-emitting assembly, the required drive current for the same example LED to provide irradiance of 50 microwatts/cm$^2$ would increase to approximately 5.5 mA. This means that the corresponding time to empty a fully-charged battery in a typical mobile communication device would be at least approximately 400 hours when using a resistor as an LED current regulator. In some examples, using a current regulator device in place of the resistor would further reduce the power drain on the battery of the mobile communication device.

FIG. 5C shows a third configuration 500c in which a light patch 506 is centered around the face of the subject. Compared to the first configuration 500a and the second configuration 500b, the third configuration 500c trades optical efficiency for a greater tolerance in terms of the light being emitted to the precise location of the eyes of the subject. The third configuration 500c may also maintain tolerance during either a portrait or landscape orientation viewing of the display of the mobile communication device 110 without having to re-locate the light-emitting assembly to a different position of the mobile communication device 110.

In order to create the light patch 506 shown in the third configuration 500c from FIG. 5C, a beam divider is also removed from the system 200 shown in FIG. 2. Similar to the second configuration 500b from FIG. 5B, a diffuser (e.g., the optical diffuser 210 shown in FIG. 2) is selected to provide a symmetrical characteristic that broadens the single LED image in two orthogonal directions to create the light patch 506 with the required width at a distance of approximately 30 cm. Assuming the light patch 506 with dimensions of approximately 16 cm×16 cm is projected at a distance 30 cm away from the light-emitting assembly, the required drive current for the same example LED to provide irradiance of 50 microwatts/cm$^2$ would increase to approximately 23.5 mA. This means that the corresponding time to empty a fully-charged battery of a mobile communication device would be approximately 95 hours using a resistor as an LED current regulator. In some examples, using a current regulator device in place of the resistor would further reduce the power drain on the battery of the mobile communication device.

In all of the configurations 500a, 500b, 500c shown in FIGS. 5A-5C, the light patch should be of substantially uniform intensity in order to optimize maintenance of a consistent level of light therapy in the event of an imperfect alignment of the light patch with the eyes of the subject. Generally, the face of the subject is at a distance of approximately 30 cm from the front of the mobile communication device 110. At a distance of approximately 30 cm, the overall dimensions of the light patches should not exceed the average dimensions of a human face or approximately 20 cm. In some examples, the light patch is sharply defined with very little light scattered into a wide angle. This is important because any light that travels past the head of the subject may be distracting for other people in the vicinity of the subject.

Figure 6:
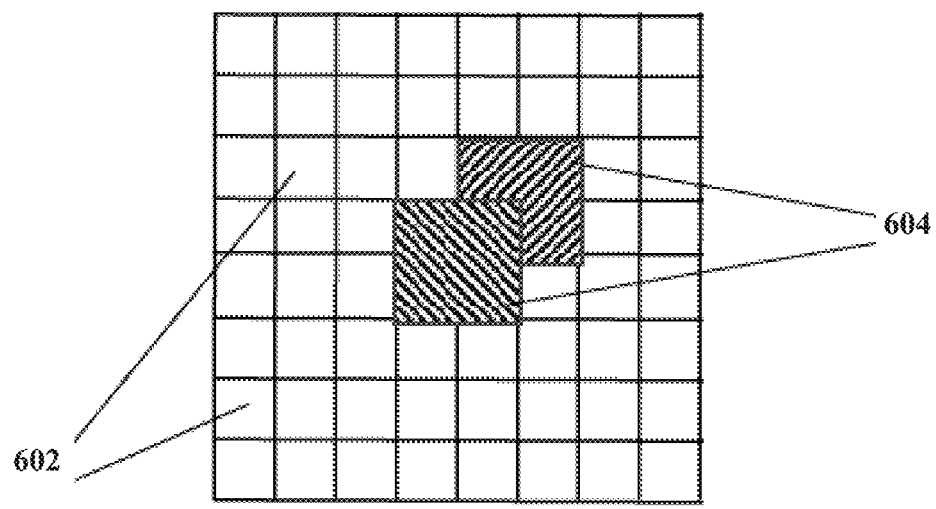
FIG. 6 is a diagram illustrating an example of an activation of distinct sub-groups of elements in an LED array to simulate lateral movement of a single larger LED element in accordance with various aspects of the present disclosure.

FIG. 6 shows an example 600 of an activation of distinct sub-groups of elements in an LED array to simulate lateral movement of a single larger LED element in accordance with various aspects of the present disclosure. While pertinent features are shown, those of ordinary skill in the art will appreciate from the present disclosure that various other features have not been illustrated for the sake of brevity and so as not to obscure more pertinent aspects of the example implementations disclosed herein. As shown in the example 600 from FIG. 6, an addressable array of small LEDs 602 may be activated in distinct subgroups 604 in order to simulate lateral movement of a single larger LED element relative to the lens.

In order to maintain ocular safety during prolonged visual exposure, constraints on the minimum area of the light-emitting aperture must be imposed. For instance, if the area of the light-emitting aperture is too small, then the radiance of the light-emitting aperture can exceed recommended safety limits. Calculations based on the current safety standards show that delivering irradiance of 50 microwatts per cm$^2$ of blue light at a distance of 30 cm from a light-emitting aperture 30 mm in diameter is safe for ocular exposure of unlimited time duration. Increasing the light-emitting aperture diameter to 45 mm allows a safe increase of irradiance at a distance of 30 cm to approximately 125 microwatts per cm$^2$ with no increase in perceived visual glare. In addition, increasing the diameter of the light aperture for a given irradiance at a distance of 30 cm may also reduce the perceived visual glare from the light-emitting aperture.

Figure 7:
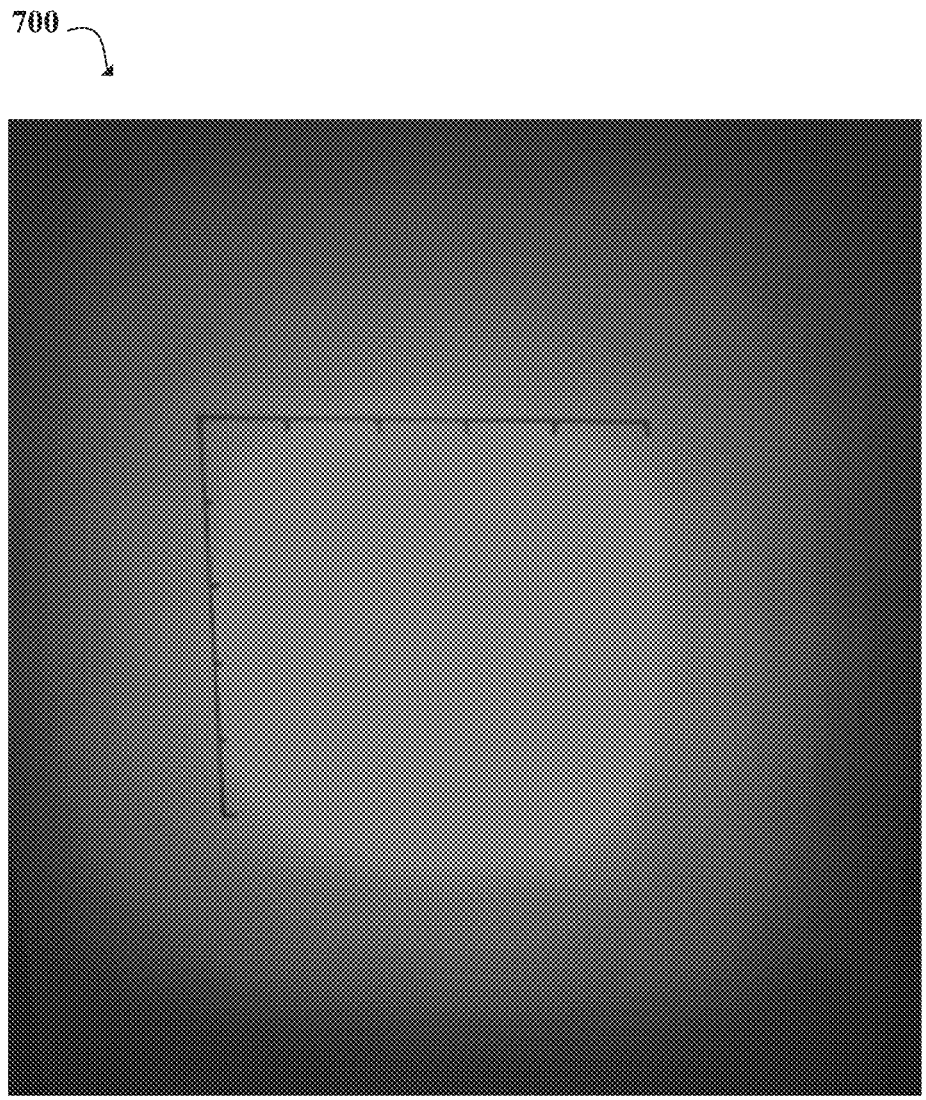
FIG. 7 is a diagram illustrating an example of a shape of a patch of light projected by a mobile ocular light therapy device in accordance with various aspects of the present disclosure.

FIG. 7 is a diagram illustrating an example 700 of a shape of a patch of light projected by a mobile ocular light therapy device in accordance with various aspects of the present disclosure. While pertinent features are shown, those of ordinary skill in the art will appreciate from the present disclosure that various other features have not been illustrated for the sake of brevity and so as not to obscure more pertinent aspects of the example implementations disclosed herein.

As shown in the example 700 from FIG. 7, the scale ticks are at approximately 25 mm intervals. The width of the patch of light at 50% of maximum intensity is 10.5 cm, which corresponds to an angular width at 50% intensity of approximately 20 degrees. The width of the patch of light at 20% of maximum intensity is 14.5 cm and the width at 10% of maximum intensity is 18.5 cm. The low intensity of light scattered into much wider angles is unlikely to cause a distraction for other persons in the vicinity of the subject using the light therapy device. In addition, unwanted wide-angle scattered light can be blocked by additional optical components with a restricted angular transmission characteristic that are mounted at the front of the light-emitting assembly.

As an example, a light-emitting assembly of the mobile ocular light therapy device is 40 mm in diameter and 14 mm in depth with a light-emitting aperture 28 mm in diameter. In this example, the light-emitting assembly incorporates a single Royal Blue LED with a current set at approximately 4.5 mA using a 560 Ohm resistor in conjunction with the 5V supply from the phone. At a drive current of 4.5 mA, the emission spectrum from the LED peaks at a wavelength of 454.5 nm. A Fresnel lens of focal length 6 mm and diameter 30 mm collects and focuses the radiation emitted by the LED, and an efficient micro-lens array diffuser expands the LED image to create a large square patch of light shown in the third configuration 500a from FIG. 5C.

At a distance of 30 cm, the measured irradiance provided by the light-emitting assembly within the spectral wavelength from 435 nm to 500 nm is 48 microwatts/cm$^2$. On the basis of calculations in accordance with International Commission on Non-Ionizing Radiation Protection (ICNIRP) guidelines, the emitted light is safe for ocular exposure of unrestricted duration.

In some examples, a higher level irradiance can be provided with equivalent ocular safety by enlarging the aperture of the light-emitting assembly. For example, a light-emitting aperture 45 mm in diameter would allow an increase in irradiance to at least 125 microwatts/cm$^2$ with no increase in visual glare and no reduction in ocular safety for unrestricted ocular exposure.

For maximum optical efficiency, the light-emitting aperture should be circular. However, the light-emitting aperture can be of any other shape, including, but not limited to, square, rectangular, or elliptical with a small loss of optical efficiency. For some alternative light-emitting aperture shapes, optical efficiency can be maximized by incorporating several adjacent individual light-emitting apertures each with its own LED source. In some examples, the light-emitting assembly may contain up to a total of six LEDs.

Figure 8:
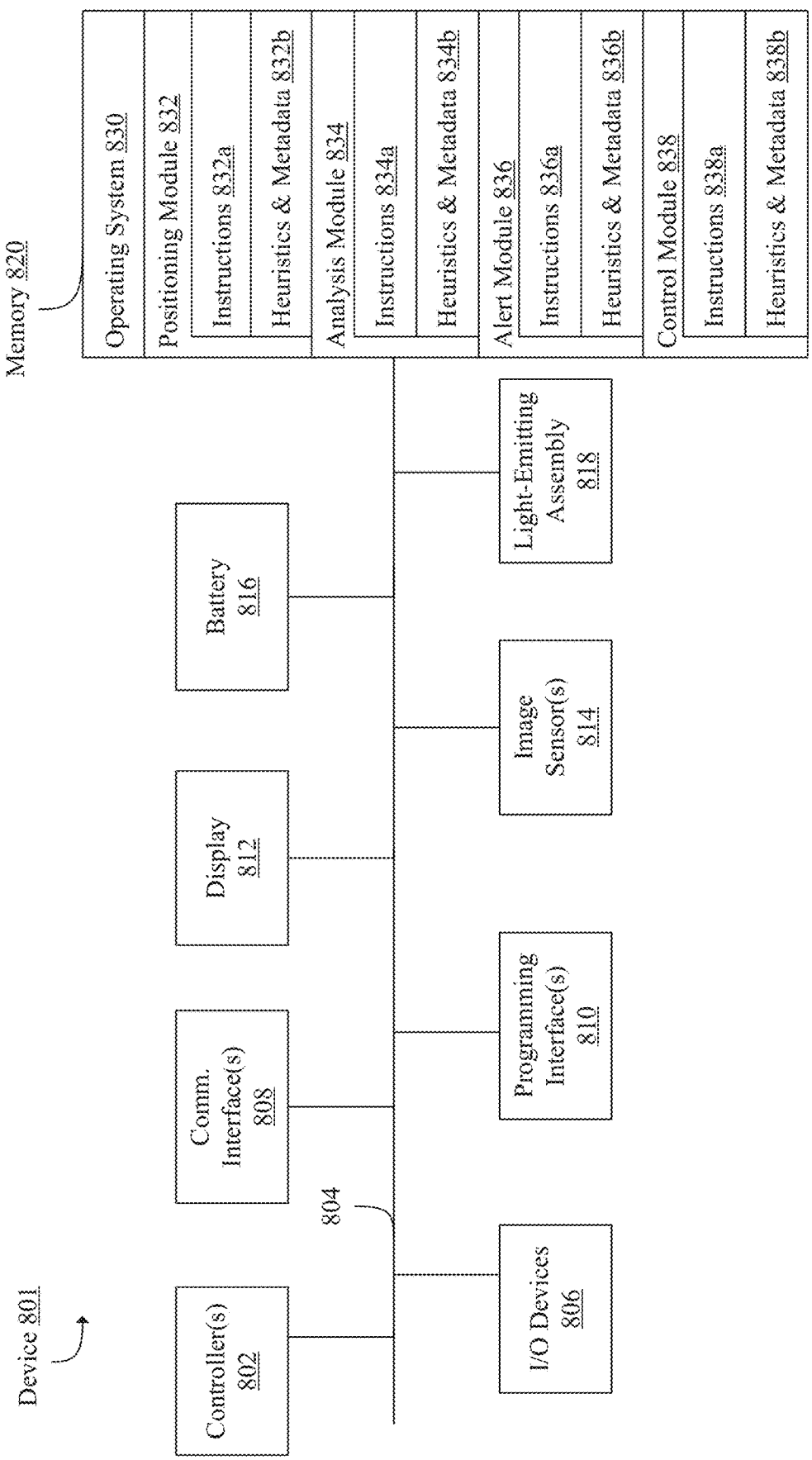
FIG. 8 is a diagram illustrating an example of a hardware implementation for an exemplary system in accordance with various aspects of the present disclosure.

FIG. 8 is a block diagram of an example of a device 801 in accordance with some implementations. FIG. 8 shows an example of a system comprising a computing device, an ocular light therapy device for administering ocular treatment to a subject, and a mounting bracket. While certain specific features are illustrated, those of ordinary skill in the art will appreciate from the present disclosure that various other features have not been illustrated for the sake of brevity, and so as not to obscure more pertinent aspects of the implementations disclosed herein. To that end, as a non-limiting example, in some implementations the device 801 includes one or more controllers 802 (e.g., microprocessors, ASICs, FPGAs, GPUs, CPUs, processing cores, and/or the like), one or more I/O devices 806 and sensors, one or more communications interfaces 808 (e.g., USB, FIREWIRE, THUNDERBOLT, IEEE 802.3x, IEEE 802.11x, IEEE 802.16x, GSM, CDMA, TDMA, GPS, IR, BLUETOOTH, ZIGBEE, and/or the like type interfaces), one or more programming (e.g., I/O) interfaces 810, a display 812, one or more optional exterior and/or interior-facing image sensors 814, a battery 816, a light-emitting assembly 818, a memory 820, and one or more communication buses 804 for interconnecting these and various other components.

In some implementations, the one or more communication buses 804 include circuitry that interconnects and controls communications between system components. In some implementations, the one or more I/O devices 806 includes at least one of a keyboard, a mouse, a touchpad, a joystick, one or more microphones, one or more speakers, one or more image sensors, one or more displays, and/or the like. For example, data may be entered by a subject to provide data and/or parameters to the device 801 in order to vary the timing, intensity of light emissions, or to set up one or more personalized light therapy programs.

In some implementations, the display 812 is capable of presenting computer generated content to the user. For example, the displays 812 may display information such as status of light therapy program, whether the light therapy program is active, selection of light therapy programs, elapsed treatment time, time remaining for the current light therapy treatment, the accumulated light received during treatment over a selected period of time, or the like. In some implementations, the display 812 may correspond to holographic, digital light processing (DLP), liquid-crystal display (LCD), liquid-crystal on silicon (LCoS), organic light-emitting field-effect transitory (OLET), organic light-emitting diode (OLED), surface-conduction electron-emitter display (SED), field-emission display (FED), quantum-dot light-emitting diode (QD-LED), micro-electro mechanical systems (MEMS), and/or the like display types. In some implementations, the one or more displays 812 correspond to diffractive, reflective, polarized, holographic, etc. waveguide displays. For example, the device 801 includes a single display. In another example, the device 801 includes a display for each eye of the user.

In some implementations, the one or more optional exterior- and/or interior-facing image sensors 814 are configured to obtain image data frames. For example, the one or more optional exterior-facing image sensors 814 correspond to one or more RGB cameras (e.g., with a complementary metal-oxide-semiconductor (CMOS) image sensor, or a charge-coupled device (CCD) image sensor), infrared (IR) image sensors, event-based cameras, and/or the like. In some examples, the one or more optional exterior- and/or interior-facing image sensors 814 are configured to acquire and process images of the face of the subject during active use of the light-emitting assembly 818 to determine if the projected patch of light is covering or not covering the eyes of the subject. In some implementations, the battery 816 corresponds to a rechargeable battery within a housing configured to power the device 801.

In some implementations, the light-emitting assembly 818 (shown in detail in FIGS. 1A-1B and 2) may include a housing with a light-emitting aperture, at least one light emitting diode (LED) configured to emit light with a component of spectral emission in a wavelength range of 435 nm to 500 nm using at least one third of a total power emitted by the at least one LED to provide ocular light treatment therapy to a subject, and a lens configured to collect the light and project a beam of the light to the eyes of the subject viewing a display of the computing device. In some examples, the light-emitting assembly 818 includes electro-mechanical or electronic means to adjust a direction of the projected path of light from the light-emitting assembly 818 based on the positioning module 832. In some examples, the light-emitting assembly 818 may include additional electronic components to receive commands from the operating system 830 and adjust a direction of the projected patch of light to correct any alignment errors. As non-limiting examples, the electro-mechanical means to adjust the direction of the projected patch of light from the light-emitting assembly 818 include motorized mechanisms to tilt the light-emitting assembly 818 relative to the mounting bracket of the light-emitting assembly or tilt a movable part of the mounting bracket relative to a fixed part of the mounting bracket, and/or motorized mechanisms to provide relative lateral movement between the LED (e.g., the LED 204 from FIG. 2) and lens (e.g., the lens 206 from FIG. 2). In some examples, the electronic means to adjust a direction of the projected patch of light include replacement of a single LED (e.g., the LED 204 from FIG. 2) with an addressable array of small LED elements (e.g., the addressable array of small LEDS 602 shown in FIG. 6) which are activated in distinct subgroups (e.g., the subgroups 604 shown in FIG. 6) of elements of the LED array to simulate lateral movement of a single larger LED relative to the lens.

The memory 820 includes high-speed random-access memory, such as DRAM, SRAM, DDR RAM, or other random-access solid-state memory devices. In some implementations, the memory 820 includes non-volatile memory, such as one or more magnetic disk storage devices, optical disk storage devices, flash memory devices, or other non-volatile solid-state storage devices. The memory 820 optionally includes one or more storage devices remotely located from the one or more controllers 802. The memory 820 comprises a non-transitory computer readable storage medium. In some implementations, the memory 820 or the non-transitory computer readable storage medium of the memory 820 stores the following programs, modules and data structures, or a subset thereof including an operating system 830, a positioning module 832, an analysis module 834, an alert module 836, and a control module 838. In some implementations, one or more instructions are included in a combination of logic and non-transitory memory.

The operating system 830 includes procedures for handling various basic system services and for performing hardware dependent tasks. The operating system 830 may contain application software to communicate with the light-emitting assembly 818. In some examples, the application software may also control light therapy session parameters, control light therapy settings, provide light therapy session data, and/or provide light therapy session recommendations.

In some implementations, the positioning module 832 is configured to obtain a positioning of a face of a subject viewing the display 812 using one or more image sensors 814. In some implementations, the positioning module 832 is further configured to perform continuous alignment of the projected beam of light on the eyes of the subject based at least in part on the image sensors 814, the analysis module 834, the alert module 836, and the control module 838. To that end, in various implementations, the positioning module 832 includes instructions 832a and/or logic therefor, and heuristics and metadata 832b therefor.

In some implementations, the analysis module 834 is configured to determine whether the projected beam of light is covering the eyes of the subject based at least in part on the positioning on the face of the subject using one or more image sensors 814. In some implementations, the analysis module 834 is further configured to provide recommendations to the subject viewing the display of the computing device regarding light therapy session timing and duration of treatment based on the control module 838 and log usage in the memory 820. To that end, in various implementations, the analysis module 834 includes instructions 834a and/or logic therefor, and heuristics and metadata 834b therefor.

In some implementations, the alert module 836 is configured to generate an alignment error alert on the display 812 based on a determination that the projected beam of light is not covering the eyes of the subject and the analysis module 834. To that end, in various implementations, the alert module 836 includes instructions 836a and/or logic therefor, and heuristics and metadata 836b therefor.

In some implementations, the control module 838 is configured to cause at least one LED to emit light having a component of spectral emission in a spectral region with a wavelength range of 435 nm to 500 nm using at least one third of a total power emitted by the at least one LED to provide ocular light treatment therapy to a subject. In some implementations, the control module 838 is further configured to control light therapy session parameters for the light-emitting assembly. In some implementations, the control module 838 is further configured to store light therapy session parameters in the usage log in the memory 820. In some implementations, the control module 838 is further configured to control the LED to emit light to provide ocular light treatment therapy to the subject for a time period longer than an hour. To that end, in various implementations, the control module 838 includes instructions 838a and/or logic therefor, and heuristics and metadata 838b therefor.

Although the positioning module 832, the analysis module 834, the alert module 836, and the control module 838 are shown as residing on a single device 801, it should be understood that in some implementations, any combination of the positioning module 832, the analysis module 834, the alert module 836, and the control module 838 may be located in separate systems or computing devices.

Moreover, FIG. 8 is intended more as a functional description of the various features that could be present in a particular implementation as opposed to a structural schematic of the implementations described herein. As recognized by those of ordinary skill in the art, items shown separately could be combined and some items could be separated. For example, some functional modules shown separately in FIG. 8 could be implemented in a single module and the various functions of single functional blocks could be implemented by one or more functional blocks in various implementations. The actual number of modules and the division of particular functions and how features are allocated among them will vary from one implementation to another and, in some implementations, depends in part on the particular combination of hardware, software, and/or firmware chosen for a particular implementation.

Light therapy has been proven to be effective for preventive light therapy and for treatment of light-related problems such as circadian rhythm problems, seasonal affective disorders, forms of depression, sleep disorders, jet lag, post-partum depression, ante-partum depression, pre-menstrual syndrome, late luteal phase, dysphonic disorder (LLPPD), bulimia, eating disorders, and chronic fatigue.

As described, the light therapy apparatus utilizes a computing device to create a projected beam of light suitable for efficient delivery of ocular light therapy to a subject using the computing device. Specifically, light therapy may be provided to the subject while the subject is viewing their computing device by emitting therapeutically effective light at a lower intensity for a longer period of time, which would solve power consumption issues in related light therapy systems. In addition, the light therapy apparatus has a high optical efficiency, low power consumption, and is packaged in a small size such that the light therapy apparatus may be removably attached to any type of computing device.

The previous description is provided to enable one of ordinary skill in the art to practice the various aspects described herein. Various modifications to these aspects will be readily apparent to those having ordinary skill in the art, and the generic principles defined herein may be applied to other aspects. Thus, the claims are not intended to be limited to the aspects shown herein, but are to be accorded the full scope consistent with the language. Thus, the language employed herein is not intended to limit the scope of the claims to only those aspects shown herein, but is to be accorded the full scope consistent with the language of the claims.

Unless otherwise indicated, all numbers expressing a characteristic, item, quantity, parameter, property, term, and so forth used in the present specification and claims are to be understood as being modified in all instances by the term "approximately." As used herein, the term "approximately" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. At the very least, and not as an attempt to limit the application of the doctrine of equivalents to the scope of the claims, each numerical indication should at least be construed in light of the number of reported significant digits and by applying ordinary rounding techniques.

Use of the terms "may" or "can" in reference to an embodiment or aspect of an embodiment also carries with it the alternative meaning of "may not" or "cannot." As such, if the present specification discloses that an embodiment or an aspect of an embodiment may be or can be included as part of the inventive subject matter, then the negative limitation or exclusionary proviso is also explicitly meant, meaning that an embodiment or an aspect of an embodiment may not be or cannot be included as part of the inventive subject matter. In a similar manner, use of the term "optionally" in reference to an embodiment or aspect of an embodiment means that such embodiment or aspect of the embodiment may be included as part of the inventive subject matter or may not be included as part of the inventive subject matter. Whether such a negative limitation or exclusionary proviso applies will be based on whether the negative limitation or exclusionary proviso is recited in the claimed subject matter.

Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

The terms "a," "an," "the" and similar references used in the context of describing the present invention (especially in the context of the following claims) are to be construed to cover both the singular and the plural, unless otherwise indicated herein or clearly contradicted by context. Further, ordinal indicators—such as "first," "second," "third," etc.— for identified elements are used to distinguish between the elements, and do not indicate or imply a required or limited number of such elements, and do not indicate a particular position or order of such elements unless otherwise specifically stated. All methods described herein can be performed in any suitable order unless otherwise indicated herein or otherwise clearly contradicted by context. The word "exemplary" is used herein to mean "serving as an example, instance, or illustration." Any aspect described herein as "exemplary" is not necessarily to be construed as preferred or advantageous over other aspects. The use of any and all examples, or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

When used in the claims, whether as filed or added per amendment, the open-ended transitional term "comprising" (and equivalent open-ended transitional phrases thereof like including, containing and having) encompasses all the expressly recited elements, limitations, steps and/or features alone or in combination with unrecited subject matter; the named elements, limitations and/or features are essential, but other unnamed elements, limitations and/or features may be added and still form a construct within the scope of the claim. Specific embodiments disclosed herein may be further limited in the claims using the closed-ended transitional phrases "consisting of" or "consisting essentially of" in lieu of or as an amended for "comprising." When used in the claims, whether as filed or added per amendment, the closed-ended transitional phrase "consisting of" excludes any element, limitation, step, or feature not expressly recited in the claims. The closed-ended transitional phrase "consisting essentially of" limits the scope of a claim to the expressly recited elements, limitations, steps and/or features and any other elements, limitations, steps and/or features that do not materially affect the basic and novel characteristic(s) of the claimed subject matter. Thus, the meaning of the open-ended transitional phrase "comprising" is being defined as encompassing all the specifically recited elements, limitations, steps and/or features as well as any optional, additional unspecified ones. The meaning of the closed-ended transitional phrase "consisting of" is being defined as only including those elements, limitations, steps and/or features specifically recited in the claim whereas the meaning of the closed-ended transitional phrase "consisting essentially of" is being defined as only including those elements, limitations, steps and/or features specifically recited in the claim and those elements, limitations, steps and/or features that do not materially affect the basic and novel characteristic(s) of the claimed subject matter. Therefore, the open-ended transitional phrase "comprising" (and equivalent open-ended transitional phrases thereof) includes within its meaning, as a limiting case, claimed subject matter specified by the closed-ended transitional phrases "consisting of" or "consisting essentially of." As such embodiments described herein or so claimed with the phrase "comprising" are expressly or inherently unambiguously described, enabled and supported herein for the phrases "consisting essentially of" and "consisting of."

All patents, patent publications, and other publications referenced and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Lastly, the terminology used herein is for the purpose of describing particular embodiments only, and is not intended to limit the scope of the present invention, which is defined solely by the claims. Accordingly, the present invention is not limited to that precisely as shown and described.

What is claimed is:

1. An apparatus configured to be coupled to a hand-held computing device to project a beam of light to provide ocular light therapy to a subject viewing a display of the hand-held computing device, comprising:
   a light-emitting assembly comprising;
      a housing with a light-emitting aperture,
      at least one light emitting diode (LED) device configured to emit light having a component of spectral emission in a spectral region with a wavelength range of 435 nm to 500 nm, wherein at least one third of total power emitted by the at least one LED device is in the spectral region,
      a lens configured to collect the emitted light from the at least one LED device and form and focus an enlarged image of the at least one LED device and project a beam of the emitted light comprising the enlarged image through the light-emitting aperture onto eyes of a subject viewing a display of the hand-held computing device, wherein at a distance of 30 cm from the light-emitting aperture the beam of light projected onto the eyes of the subject has a height and a width of less than 20 cm measured between the points on the beam where an intensity of the beam is half of a maximum intensity of the beam; and an electronic component configured to receive commands from the hand- held computing device;

application software loadable onto the hand-held computing device, the application software being configured to communicate with the electronic component of the light-emitting assembly and further configured to perform at least one function selected from the group consisting of: controlling light therapy session parameters, controlling light therapy settings, storing light therapy session parameters in a usage log and providing light therapy session data and/or light therapy session recommendations via a user interface of the hand-held computing device; and a mounting bracket attached to the housing and configured to be removably attached to the hand-held computing device or a case of the hand-held computing device.

2. The apparatus of claim 1, further comprising:
a power receiver configured to receive power for the apparatus from the hand-held computing device.

3. The apparatus of claim 1, further comprising:
a rechargeable battery within the housing configured to power the apparatus.

4. The apparatus of claim 1, wherein the lens is further configured to project the beam of the light by projecting a first beam of light onto a first eye of the subject and a second beam of light onto a second eye of the subject.

5. The apparatus of claim 1, wherein the light-emitting assembly further comprises:
a beam divider configured to split the projected beam of the light into a first beam of light projected onto a first eye of the subject and a second beam of light projected onto a second eye of the subject.

6. The apparatus of claim 1, wherein the light-emitting assembly further comprises:
an optical diffuser configured to diffuse the projected beam of the light along a horizontal direction.

7. The apparatus of claim 1, wherein the light-emitting assembly further comprises:
an optical diffuser configured to diffuse the projected beam of the light along a horizontal direction and a vertical direction.

8. The apparatus of claim 1, wherein the light-emitting assembly is further configured to emit the light to provide an irradiance within a range of 50 to 200 microwatts/cm$^2$ in a spectral region with the wavelength range of 435 nm to 500 nm at the distance of 30 cm from the light-emitting aperture.

9. The apparatus of claim 1, wherein the at least one LED device comprises six or less LEDs.

10. A system, comprising:
a hand-held computing device; and
the apparatus for administering ocular light treatment to a subject according to claim 1.

11. The system of claim 10, wherein the hand-held computing device comprises a controller, an image sensor, and the display, wherein the controller is configured to:
obtain a positioning of a face of the subject viewing the display using the image sensor; and
generate an alignment error alert on the display based on a determination that the projected beam of the light is not covering the eyes of the subject based at least in part on the positioning of the face.

12. The system of claim 11, wherein the controller is further configured to:
perform continuous alignment of the projected beam of the light on the eyes of the subject based at least in part on the alignment error.

13. The system of claim 10, further comprising a controller and memory, wherein the controller is configured to:
control light therapy session parameters for the light-emitting assembly,
store light therapy session parameters in a usage log in the memory; and
provide recommendations to the subject viewing the display of the hand-held computing device regarding light therapy session timing and duration of treatment based on the light therapy session parameters and log usage in the memory.

14. The system of claim 10, further comprising a controller configured to:
control the at least one light emitting diode (LED) device to emit light to provide ocular light treatment therapy to the subject for a time period longer than an hour.

15. The apparatus of claim 1, wherein the at least one function is to start or stop a light therapy session or to adjust the intensity or the spectrum of the emitted light.

16. The apparatus of claim 1, wherein the light-emitting assembly further comprises: remotely-controllable electro-mechanical or electronic means to adjust the direction of the projected beam of light from the light-emitting assembly in response to commands from the hand-held computing device.

17. The apparatus of claim 16, wherein the commands from the hand-held computing device originate from a determination by the application software on the hand-held computing device that the projected beam of the light is not covering the eyes of the subject based at least in part on processing of images of the face of the subject acquired by an image sensor of the hand-held computing device during active use of the light-emitting assembly by the subject.

* * * * *